United States Patent [19]

Fabinski et al.

[11] 4,373,137

[45] Feb. 8, 1983

[54] RADIATION DETECTION AND RECEIVING IN NONDISPERSIVE INFRARED GAS ANALYZER

[75] Inventors: Walter Fabinski, Kriftel; Udo Deptolla, Ober-Olm; Margareta Ascherfeld, Oberursel, all of Fed. Rep. of Germany

[73] Assignee: Hartmann & Braun Aktiengesellschaft, Frankfurt am Main, Fed. Rep. of Germany

[21] Appl. No.: 159,115

[22] Filed: Jun. 13, 1980

[30] Foreign Application Priority Data

Jun. 20, 1979 [DE] Fed. Rep. of Germany ....... 2924843

[51] Int. Cl.³ .............................................. G01J 1/00
[52] U.S. Cl. ................................... 250/343; 250/344; 250/352
[58] Field of Search ............... 250/343, 344, 345, 346, 250/347, 353, 352; 356/437

[56] References Cited

U.S. PATENT DOCUMENTS

| | | | |
|---|---|---|---|
| 2,550,419 | 4/1951 | Martin | 250/343 |
| 4,210,808 | 7/1980 | Miyatake | 250/343 |
| 4,281,248 | 7/1981 | Fabinski et al. | 250/343 |

Primary Examiner—Alfred E. Smith
Assistant Examiner—Janice A. Howell
Attorney, Agent, or Firm—Ralf H. Siegemund

[57] ABSTRACT

The chopped infrared radiation leaving a measuring and sample gas chamber in an infrared gas analyzer is passed through and into two serially arranged detection chambers which are connected to a differential pressure chamber with capacitive pickup. The chambers are filled with gas of the type whose concentration, in the sample gas, is to be detected. One of the detector chambers contains a thin black wire, a diaphragm on the outside may shield an adjustable portion of that wire from radiation. The wire absorbs all radiation it intercepts and heats the environment.

3 Claims, 3 Drawing Figures

RADIATION DETECTION AND RECEIVING IN NONDISPERSIVE INFRARED GAS ANALYZER

BACKGROUND OF THE INVENTION

The present invention relates to nondispersive infrared gas analyzers; and more particularly, the invention relates to radiation receivers and detectors for such analyzers.

Analyzers of the type to which the invention pertains use basically the principle of selective absorption. Broadband infrared radiation is selectively absorbed by the gas component to be detected in, and as part of, a sample gas; and the residual radiation of these wavelengths and band or bands is detected by means of detection chambers being filled with just that particular component. A problem arises when the sample gas contains also another gas or gases whose absorption band or bands overlap any absorption band of the component of interest. These interfering components falsify the measuring result; and the error is, of course, the greater, the larger the overlap and the higher the concentration of that interfering component. The problem has been dealt with in various ways.

A particular method and apparatus for measuring the concentration of particular components in a carrier gas has been described, for example, in U.S. Pat. Nos. 3,162,761 and 2,951,939. Particularly, the latter patent includes a suggestion to provide a special filter being strata of gases of the type that produces the interference problem. This particular filter removes the overlapping band portions from the analysis. U.S. Pat. No. 3,925,667 suggests another approach and U.S. Pat. Nos. 3,725,702 and 4,156,812 deal with null-point shifts generally.

DESCRIPTION OF THE INVENTION

It is an object of the present invention to improve the frequency selectivity and, therefore, the sensitivity of infrared gas analysers.

It is a particular object of the present invention to improve the detection of chopped infrared radiation which has passed through a chamber containing sample gas which includes a component to be detected as well as one or more interfering components having one or more infrared absorption bands, overlapping one or more absorption bands of the component to be detected.

In accordance with the preferred embodiment of the invention, a detector assembly is adopted, known per se, and including a front chamber or cell and a rear chamber or cell both filled with gas of the type whose presence and concentration is to be detected in the sample gas. Both detection chambers or cells are connected to a differential pressure chamber with capacitive pickup. Specifically, it is now suggested that one of these chambers is to include thin element means such as one or more wires which intercept and absorb infrared radiation in a nonfrequency-selective manner. Also, the wire or wires are to have a small heat capacity and act, in fact, as blackbody absorbers. Preferably a diaphragm may be positioned in front of the chamber containing this wire or the like, in order to partially block off radiation therefrom and in an adjustable fashion. It was found that one can optimize the attenuation or suppression of the effect the interfering gas component has on the measuring result by proper trial-and-error adjustment of that diaphragm. The choice of placement of the blackbody element, i.e., whether in the front or in the rear detection chamber depends upon circumstances. For example, measuring the $SO_2$ concentration in a carrier gas in the presence of water vapor makes it advisable to place the element (wire) in the rear chamber. In the case of measuring the CO concentration in the presence of $CO_2$, the wire should be placed into the front chamber.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

Proceeding now to the detailed description of the drawings, FIG. 1 illustrates a source S of infrared radiation, represented by arrows and being periodically interrupted by a motor-driven chopped disk or diaphragm M. The chopped infrared beam traverses a cell, chamber, or cuvette 7, being flown through by sample or measuring gas containing a particular component to be detected, but possibly containing also an interfering gas having an absorption band or bands overlapping an absorption band or bands of the particular component. The infrared radiation is frequency-selectively absorbed by the content of sample chamber 7 and to an extent depending upon the concentrations of the absorbing gases.

Figure 1:
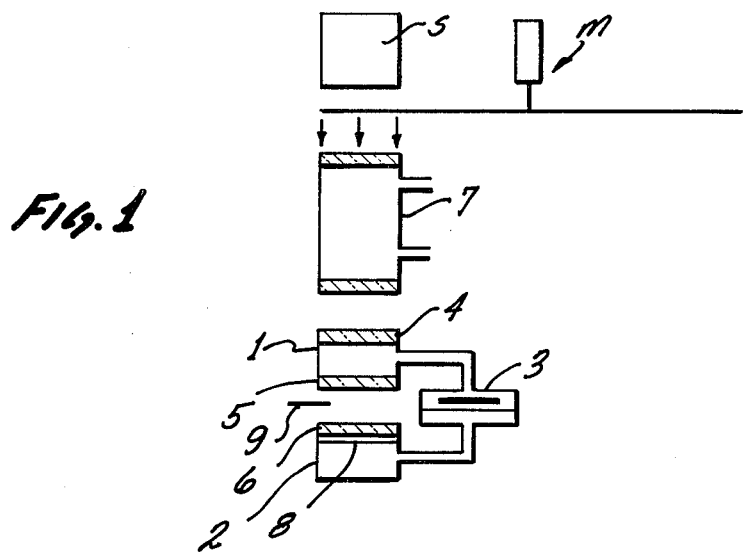
FIG. 1 is a schematic view of a first example of the preferred embodiment for practicing the best mode of the invention as applied to a single beam-path-type infrared analyzer.

Radiation exiting from chamber 7 traverses a first detection chamber 1, having an entrance window 4 and an exit window 5. The radiation continues to a second detection chamber 2, having an entrance window 6, but no exit window. The two chambers 1 and 2 are thus disposed downstream from the sample chamber 7 and are serially traversed by the radiation which leaves chamber 7.

The two chambers 1 and 2 are connected to a differential pressure chamber 3 being partitioned by a flexible membrane which is one electrode of a capacitor. This capacitor constitutes a pickup from which an electric signal is derived indicating the concentration of the component of interest, in the sample gas. Details of this pickup have been omitted; see the references mentioned above.

The rear or second chamber 2 contains, in addition, one or more thin wires 8 having a black surface. This blackbody-type wire has a very low heat capacity, i.e., it absorbs all radiation it intercepts and reradiates as well as conductively emits heat at a very high rate. The absorption by wire 8 is not frequency selective, but pulsates in accordance with the interruptions of the radiation beam by the chopper. Accordingly, the heat transfer from wire 8 to its environment is also a periodically variable one.

It was found that this supplemental heating of the rear chamber reduces the effect of an interfering component.

In particular, if the content of $SO_2$ in a carrier gas is to be detected, chambers 1 and 2 are filled with $SO_2$. The sample gas may, however, include water vapor. Water and $SO_2$ have overlapping absorption bands. The supplemental pulsating heating of chamber 2 by means of the nonfrequency-selective absorption of a portion of the radiation by wire 8 augments the pulsating frequency-selective absorption in both chambers 1 and 2 in such a way that the unwanted attenuation of the radiation in chamber 7 by any water vapor, in the range of the $SO_2$ absorption bands, is largely suppressed.

It was found practical to provide a simple diaphragm 9 for attenuating the radiation before reaching rear chamber 2.

This diaphragm is particularly constructed as a needle in order to block some of that portion of the radiation that would otherwise reach wire 8. It was found that this feature permits in situ adjustment toward optimizing the suppression of $H_2O$-induced errors.

Figure 2:
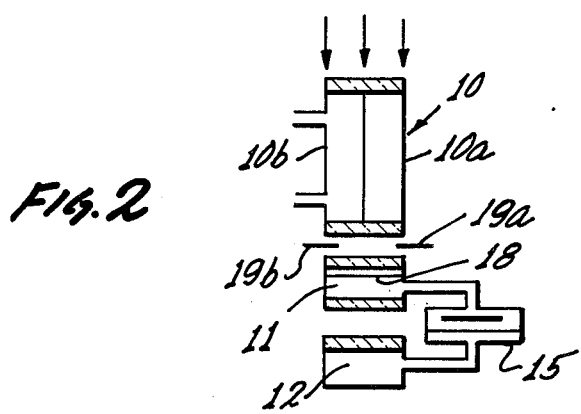
FIG. 2 is a schematic view of another example for practicing the invention in a two-beam analyzer.

FIG. 2 illustrates a two-beam instrument. A cuvette 10, receiving the infrared beams and being traversed by them, is partitioned into two chambers. One part, chamber 10a, contains a reference gas, the other part, chamber 10b, is flown through by a sample gas. The reference gas may contain a specific quantity of the gas component to be detected.

The two beams, being differently attenuated, reach a first chamber, 11, across which is placed one or more of the absorbing wires 18. The portion of the radiation not yet absorbed will reach the rear chamber 12. Adjustable diaphragms 19a and 19b trim individually the respective radiation portions and their cross sections to adjust the respective beam portions permitted to proceed after leaving cuvette 10. Chambers 11 and 12 are both connected to a differential chamber 15 with capacitive pickup. The nonfrequency-selective absorption by the wire and the immediate periodic heating of the surrounding gas reduces also here the effect of absorption by an interfering gas in chamber 10b. The wire or wires 18 do not have to intercept the reference beam, in which case diaphragm 19a could be omitted. However, for reasons of symmetry and ease of optimization, the wire should intercept both beams equally.

Figure 3:
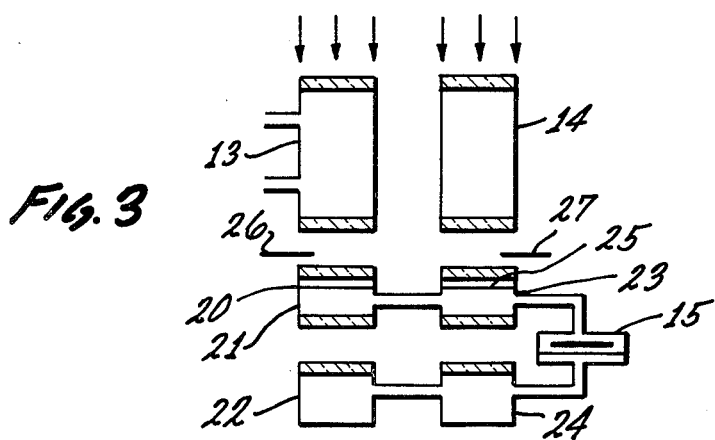
FIG. 3 is a further example for a two-beam analyzer, functionally similar to, but structurally different from, the analyzer shown in FIG. 1.

The analyzer depicted in FIG. 3 does not differ from the one of FIG. 2 in basic operation. The differences reside in the structure; the two beam paths are separated to a greater extent, and there is a two-cell detection assembly for each path. Accordingly, separate cells and chambers are provided for the sample gas (cell 13) and for the reference gas (14). The measuring path includes two serially effective detection cells: 21, 22, of which the front cell, 21, contains a black wire 20. The reference path includes detection cells 23 and 24, and the front cell, 23, contains also a black wire 25, which is optional. The front cells 21 and 23 are gas-conductively interconnected; so are the rear cells 22 and 24. Front and rear cells connect to opposite sides of the differential chamber 15 with capacitive pickup including a flexible partitioning membrane. The pickup is of the same type mentioned above. Also, the system includes adjustable diaphragms 26 and 27 for blocking off part of the radiation that would otherwise reach the wires 20 and 25, respectively.

The analyzers of FIGS. 2 and 3 can be used, for example, for detecting the CO content in a carrier gas. $CO_2$ may also be present and constitutes an interfering component because CO and $CO_2$ have overlapping absorption bands. The arrangement does, however, significantly attenuate the effect $CO_2$ would have otherwise on the measuring result.

It should be noted that the wires, such as wires 8, 18, 20, and/or 21, may be flat and turnable in order to adjust from the outside, the effective cross section such wire offers to the incoming radiation. In such a case, one may not need the respective diaphragm.

The invention is not limited to the embodiments described above; but all changes and modifications thereof, not constituting departures from the spirit and scope of the invention, are intended to be included.

We claim:

1. In a nondispersive infrared gas analyzer having at least one path for a periodically interrupted beam of infrared radiation traversing a chamber for sample gas which contains a particular component to be detected as well as an interfering component, the analyzer further including a differential pressure-measuring chamber with capacitive pickup, one of the electrodes of the pickup being a flexible membrane partitioning the differential pressure-measuring chamber, the improvement comprising in combination:

a front detection chamber and a rear detection chamber disposed in said path downstream from said sample gas chamber and being serially traversed by radiation, the front chamber and rear chamber being connected to the differential measuring-chamber at opposite sides of the membrane, the front and rear chambers being filled with said particular component, one of the front and rear chambers containing a thin, nonfrequency-selective, absorbing element having a small heat capacity and intercepting a small portion of the radiation reaching the particular chamber in which it is contained.

2. The improvement as in claim 1, the element being at least one black wire.

3. The improvement as in claim 1 or 2, and including an adjustable diaphragm disposed in front of the particular chamber containing the element.

* * * * *